US00PP31486P2

(12) United States Plant Patent
Hansen

(10) Patent No.: US PP31,486 P2
(45) Date of Patent: Feb. 25, 2020

(54) ***PHLOX* PLANT NAMED 'ROCKY ROAD PINK'**

(50) Latin Name: ***Phlox* hybrid**
Varietal Denomination: Rocky Road Pink

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/350,917

(22) Filed: Feb. 1, 2019

(51) Int. Cl.
*A01H 5/02* (2018.01)
*A01H 6/70* (2018.01)

(52) U.S. Cl.
USPC ..... Plt./320

(58) Field of Classification Search
USPC ..... Plt./320
See application file for complete search history.

*Primary Examiner* — Susan McCormick Ewoldt

(57) ABSTRACT

A unique cultivar of Hybrid Spring *Phlox* named *Phlox* 'Rocky Road Pink' characterized by vigorous, dense, multi-stemmed, winter-hardy habit with short, bright glossy-green, linear leaves. Flowering begins in mid-April and continuing for nearly five weeks on heavily-branched peduncles and completely cover the plant in peak season. Petals are bright rosy-pink with a small dark-purple eye. Petal apices are moderately notched. The new plant is able to withstand dry conditions once established, and the foliage stays clean and resists mildew. The new plant is especially suitable for the landscape as a potted plant and in the garden as a specimen or en masse.

1 Drawing Sheet

Botanical classification: *Phlox* hybrid.
Variety denomination: 'Rocky Road Pink'.

STATEMENT REGARDING PRIOR DISCLOSURES UNDER 37 CFR 1.77(B)(6)

The first public disclosure of the claimed plant, in the form of a photograph and brief description on a website operated by Walters Gardens, Inc. on Feb. 1, 2018. The claimed plant was first sold on Jul. 10, 2018 by Walters Gardens, Inc., who obtained the plant and all information relating thereto, from the inventor. No plants of *Phlox* 'Rocky Road Pink' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of *Phlox* plant, known as *Phlox* 'Rocky Road Pink' and will be referred to hereafter by its cultivar name, 'Rocky Road Pink', or the "new plant". The new plant was hybridized by the inventor at a wholesale perennial nursery in Zeeland, Mich. on Mar. 31, 2014 as cross between *Phlox subulata* 'Emerald Blue' (not patented) as the female parent times *Phlox douglasii* 'Cracker Jack' (not patented) as the male parent. The new plant passed initial evaluation on the spring of 2016 and was assigned the breeder code 14-326-1 through the remaining evaluation process. 'Rocky Road Pink' was first asexually propagated by stem cuttings in the greenhouses at the same nursery in Zeeland, Mich. in the summer of 2016. The unique characteristics of the new plant have been found to be reproducible and stable in successive generations of asexually propagated and the resultant plants have been found to be identical to the original selection.

BRIEF SUMMARY OF THE PLANT

*Phlox* 'Rocky Road Pink' is unique from all other Hybrid Spring *Phlox* known to the inventor. The nearest comparison plants known to the inventor include: the female and male parents, 'Red Wing' (not patented) and the copending cultivar 'Rocky Road Magenta'. 'Plumtastic' U.S. Plant Pat. No. 28,896 has flowers have a distinct white eye upon opening with a deep blue-violet color on the outside of the petals. 'Strawberries and Cream' U.S. Plant Pat. No. 28,762 has lighter pink flowers that change significantly to near white. 'Red Wing' has flowers of bright crimson-pink, more vigorous growth. The female parent, 'Blue Emerald', has flowers that are a delicate bluish purple with thinner and shorter foliage and more rampant growth habit. The male parent, 'Cracker Jack' has flowers that are less overlapping, magenta-red with less deeply cleft petal lobe apices. 'Rocky Road Magenta' has magenta-purple flowers and is shorter in habit.

*Phlox* 'Rocky Road Pink' differs from and all other *phlox* known to the inventor in the following repeatedly observed traits in combination:

1. Vigorous plants of dense mounded habit, spreading by rooting stems, producing short, clean, glossy, bright-green, linear leaves;
2. Multiple heavily-branched stems produce branched panicles;
3. Flower beginning in mid-April and continuing for nearly five weeks completely covering plant at peak flowering;

4. Flowers of bright rosy-pink with small dark-purple eye;
5. Plant is able to withstand dry conditions once established.

BRIEF DESCRIPTION OF THE DRAWINGS

The photographs of the new plant demonstrate the unique traits of *Phlox* 'Rocky Road Pink' and the overall appearance of the plant at three-years old growing in a full-sun trial bed in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
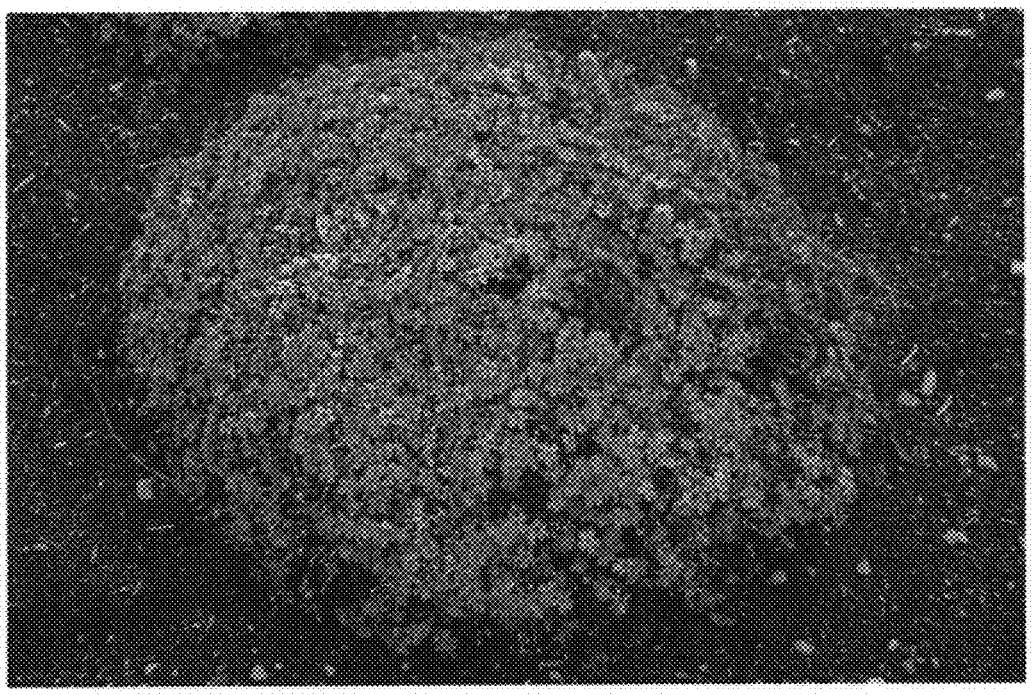
FIG. 1 shows the new plant in peak flower in the landscape.
Figure 2:
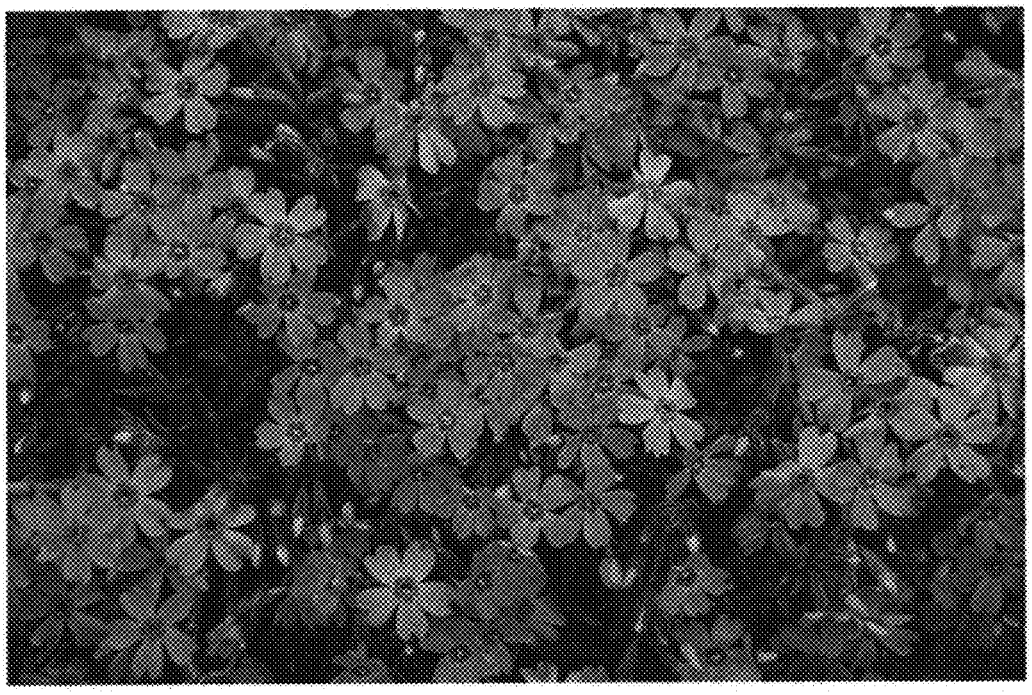
FIG. 2 shows a close-up of the flowers and buds.

The following descriptions and color references are based on the 2015 edition of The Royal Horticultural Society Colour Chart except where common dictionary terms are used. *Phlox* 'Rocky Road Pink' has not been observed under all possible environments. The phenotype may vary slightly with different growing environments such as temperature, light, fertility, soil pH, moisture and maturity levels, but without any change in the genotype. The following observations and size descriptions are based on three-year-old plants in the full-sun trial garden of a wholesale perennial nursery in Zeeland, Mich. with supplemental fertilizer and water as needed.

Botanical classification: *Phlox* hybrid;

Parentage: Female or seed parent is *Phlox subulata* 'Emerald Blue', male or pollen parent is *Phlox douglasii* 'Cracker Jack';

Plant habit: Winter-hardy, evergreen herbaceous perennial; short, dense, producing about 20 to 30 stiff, highly-branched stems; foliage to about 13.5 cm tall and 60.0 cm wide, average 12.5 cm tall and 55.0 cm wide; flowering to 17.0 cm tall and 58.0 cm wide;

Propagation: Stem cuttings; rooting in about 3 weeks;

Time to produce finished crop in 3.8 liter pots: About 8 to 12 weeks; moderately vigorous;

Root: Fibrous and freely branching; color creamy white to tan depending on soil type;

Leaves: Simple; opposite proximally, whorled distally; linear; apex apiculate; base truncate, clasping; margin entire, micro-ciliolate; lustrous and glabrous both adaxial and abaxial; about 9.0 mm long by about 2.0 mm wide, average about 8.5 mm long and 1.5 mm wide;

Leaf color: Adaxial expanding nearest RHS 137A distally and RHS 144A proximally; abaxial nearest RHS 1378; adaxial mature nearest RHS 137A and abaxial mature nearest RHS 137B;

Foliage fragrance: None detected;

Veins: Pinnate; not conspicuous adaxial and abaxial;

Vein color: Same color as surround leaf;

Petiole: Leaves sessile;

Stems: Cylindrical; flexible distally, strong near base; wiry; upright to outwardly; to 1.0 mm diameter near base and heavily-branching; surface exfoliating proximally and puberulent distally;

Stem color: Base nearest RHS 199B and distally nearest RHS 145C;

Internodes spacing: Proximally about 4.2 mm; distally less than 1.0 mm; average about 1.2 mm;

Node color: Color nearest RHS 183D distally and nearest RHS 199B proximally;

Inflorescence: Mostly upright; 4.5 cm tall and 3.3 cm wide; average of 4 flowers;

Flowers: Perfect; salverform; mostly flat faced; about 18.0 mm across face and 15.0 mm long; with fused corolla tube about 14.0 mm long and 2.0 mm diameter near face; attitude upright to outwardly;

Flower longevity: About 5 days on plant; self-cleaning;

Flower fragrance: Lightly sweet;

Buds one to two days prior to opening: Narrowly oblanceolate, to narrowly clavate; bluntly acute apex with rounded base; petals implicate; about 11.0 mm long, 3.5 mm long in terminal bulb portion and 6.5 mm long in tube; tube to 1.5 mm diameter, bulb to 2.0 mm diameter;

Bud color: Nearest RHS N80D in expose petal bulb portion, exposed tube between RHS N79C and RHS N77B, calyx nearest 144A with blush of nearest RHS 183B;

Petals: Five; blade and claw base fused into tube; apex rounded and emarginate about 2.0 mm deep; blades slightly imbricate about 1.0 mm; margin entire; glabrous adaxial and abaxial;

Petal size: Blade about 8.0 mm long and 6.5 mm wide near center; tube about 14.0 mm long and 2.0 mm diameter;

Petal color:

Young adaxial: Center and distal blade nearest RHS 74B, with two 1.5 mm long striae near center eye nearest RHS 71A; basal 2.0 mm of tube nearest RHS N144D, remaining tube portion nearest RHS 75C;

Young abaxial: Center and distal blade between RHS N74C and RHS NN74C; basal tube nearest RHS N144D and remaining tube portion between RHS N79C and RHS N77B;

Mature adaxial: Center and distal blade nearest RHS 77B with striae between RHS 83A and RHS 83B; basal 2.0 mm of tube nearest RHS N144D, remaining tube portion nearest RHS 75C;

Mature abaxial: Center and distal blade nearest RHS 77B; basal tube nearest RHS N144D and remaining tube portion between RHS N79C and RHS N77B;

Androecium: Typically five;

Filaments: Five, adnate to inner corolla at various heights about 9.0 mm to 13.0 mm from base; about 1.1 mm long and 0.1 mm in diameter; color nearest RHS NN155D;

Anther: Five; oblong elliptic; basifixed; oblong, about 2.0 mm long by 1.0 mm wide; color nearest RHS 17C;

Pollen: Nearly microscopic, spherical; color nearest RHS 21A;

Gynoecium: One pistil per flower; 14.0 mm long;

Style: Cylindrical; about 11.0 mm long and 0.2 mm diameter when flower is mature; persistent after flower abscission; color nearest RHS 4D;

Stigma: Trifid in proximal 1.5 mm long, about 0.2 mm diameter; color nearest RHS 9A;

Ovary: Inferior; ellipsoidal; acute apex and truncate base; about 1.5 mm long and 1.0 mm diameter; color between RHS 144A and RHS 143A;

Calyx: Campanulate; pubescent abaxial, glabrous adaxial; about 6.0 mm long and 2.0 mm across at apex;

Sepals: Five; lanceolate; glabrous adaxial and pubescent abaxial; narrowly acute apex, fused in basal 4.0 mm; margin entire; pubescent abaxial, glabrous and lustrous adaxial; individually about 6.0 mm long and 1.0 mm wide at fusion;

Sepal color: Adaxial between RHS 146A and RHS 146B; abaxial nearest RHS 144A and with blush of nearest RHS 183B;

Peduncle: Finely puberulent; strong, flexible; mostly upright; cylindrical; about 1.5 mm diameter at base and 1.5 cm long;

Peduncle color: Nearest RHS 144A;

Pedicle: Cylindrical; finely puberulent; flexible; upright to outwardly; variable from 5.0 mm to 18.0 mm long and 0.7 mm diameter;

Pedicle color: Variable, nearest RHS 144A with light to heavy blush of nearest RHS 183D;

Fruit and seeds: Not observed;

Hardiness and culture: The new plant grows best with full sun, light moisture and deep drainage; hardy to at least from USDA zone 4 through 8.

Disease and pest resistance: *Phlox* 'Rocky Road Pink' demonstrates excellent powdery mildew resistance under conditions that would normally show symptoms.

I claim:

1. A new and distinct cultivar of Hybrid Spring *Phlox* plant named *Phlox* 'Rocky Road Pink' as herein described and illustrated.

* * * * *